United States Patent
Gale et al.

(10) Patent No.: US 9,435,388 B2
(45) Date of Patent: Sep. 6, 2016

(54) CLUTCH MECHANISM

(71) Applicant: Freehand 2010 Limited, Peasmarsh (GB)

(72) Inventors: David Gale, Cambridgeshire (GB); Adrian Cooper, Cambridgeshire (GB); Keith Marshall, Bedfordshire (GB); Clive Francis, Berkshire (GB)

(73) Assignee: Freehand 2010 Limited, Guildford (GB)

( * ) Notice: Subject to any disclaimer, the term of this patent is extended or adjusted under 35 U.S.C. 154(b) by 0 days.

(21) Appl. No.: 14/102,409

(22) Filed: Dec. 10, 2013

(65) Prior Publication Data
US 2014/0251043 A1   Sep. 11, 2014

Related U.S. Application Data

(63) Continuation-in-part of application No. 12/415,993, filed on Mar. 31, 2009, now Pat. No. 8,622,999.

(30) Foreign Application Priority Data

Apr. 4, 2008   (GB) ..................... 0806211

(51) Int. Cl.
*A61B 17/00* (2006.01)
*F16D 43/20* (2006.01)
*F16H 25/20* (2006.01)

(52) U.S. Cl.
CPC .......... *F16D 43/20* (2013.01); *F16H 25/2021* (2013.01); *F16H 2025/2046* (2013.01); *F16H 2025/2071* (2013.01); *Y10T 74/18792* (2015.01)

(58) Field of Classification Search
CPC ... A61B 17/00; A61B 19/00; F16H 25/2021; F16H 2025/2046
USPC ..................................... 606/1, 130
See application file for complete search history.

(56) References Cited

U.S. PATENT DOCUMENTS

| 4,367,805 A | 1/1983 | Totani et al. |
| 5,006,112 A | 4/1991 | Metzner |

(Continued)

FOREIGN PATENT DOCUMENTS

| DE | 1750562 A1 | 1/1971 |
| FR | 2550177 A1 | 2/1985 |

OTHER PUBLICATIONS

European search report and search opinion dated Dec. 29, 2009 for Application No. 09157276.8.

(Continued)

*Primary Examiner* — Victor Nguyen
(74) *Attorney, Agent, or Firm* — Lewis, Reese & Nesmith, PLLC

(57) ABSTRACT

A clutch mechanism 5 for use with a carrier of a linear drive device 1, where the mechanism 5 includes: a housing 3; a first gear 6 coupled to the housing 3 and having gear teeth 61 configured to engage a threaded shaft 2 of a linear drive device 1, so that rotation of the shaft 2 causes the housing 3 to move along the shaft 2 in a first mode of operation; and a first clutch arrangement associated with the first gear 6 and configured to prevent substantial rotation of the first gear 6 with respect to the housing 3 when a rotational force applied to the first gear 6 is less than a threshold force and to permit rotation of the first gear 6 with respect to the housing 3 when a rotational force applied to the first gear 6 is greater than the threshold force. In a second mode of operation, the housing 3 can be manually moved along a length of the shaft 2 by exerting a force on the housing 2 and causing the rotational force applied to the first gear 6 through the interaction of the threaded shaft 2 and the gear teeth to exceed the first threshold.

15 Claims, 13 Drawing Sheets

(56) References Cited

U.S. PATENT DOCUMENTS

| | | |
|---|---|---|
| 8,622,999 B2 | 1/2014 | Gale et al. |
| 2001/0034533 A1* | 10/2001 | Staehlin et al. ............. 606/179 |
| 2005/0040284 A1* | 2/2005 | Christensen et al. ......... 244/101 |
| 2005/0234435 A1 | 10/2005 | Layer |
| 2009/0270880 A1 | 10/2009 | Gale et al. |

OTHER PUBLICATIONS

Office action dated Mar. 20, 2013 for U.S. Appl. No. 12/415,993.

Office action dated Jul. 4, 2012 for CN Application No. 200910130386.7.

Office action dated Aug. 16, 2012 for U.S. Appl. No. 12/415,993.

* cited by examiner

CLUTCH MECHANISM

CROSS-REFERENCE

This application is a continuation-in-part application of Ser. No. 12/415,993, filed Mar. 31, 2009, which claims priority to GB0806211.9, filed on Apr. 4, 2008, which is incorporated herein by reference in its entirety.

BACKGROUND OF THE INVENTION

1. Field of the Invention

Embodiments of the present invention relate to a clutch mechanism for use with a linear drive device, a linear drive device including such a clutch mechanism, and a surgical tool holding mechanism including such a linear drive device. Specifically, embodiments of the present invention relate to a surgical tool holding mechanism including a linear drive device and clutch mechanism.

2. Description of Related Art

Linear drive devices are known for use in various applications. Generally, these devices comprise a motor coupled to a threaded shaft and a carrier mounted on the threaded shaft. The carrier has an element which engages the thread of the shaft and the carrier is prevented from rotation about the shaft such that when the motor drives rotation of the shaft, the carrier is driven along a length of the shaft in a linear movement. Reversing the rotation of the shaft causes a reversal in the direction of the linear movement of the carrier along the shaft. Thus, a motor can be used to impart linear motion to a carrier.

An example of an application for such linear drive device is in the operation of a surgical robot or other surgical tool holding mechanism to drive a zoom motion of an endoscope mounted on the carrier of the device—in other words, to move an endoscope or endoscopic instrument into and out of a surgical site.

Linear drive devices used in applications such as surgical robotics (and the like) are often configured to drive the carrier at a low speed—for example, for safety reasons. If a large movement is required, then it is convenient for faster movement of the carrier to be permitted. This may be achieved by providing an actuator coupled to the element of the carrier. The actuator, when activated, causes the element to disengage the thread of the threaded shaft of the linear drive device. The carrier is, therefore, free to be manually moved along the length of the threaded shaft without requiring rotation of the shaft itself. When the carrier has been moved to the desired location along the length of the shaft, the actuator is deactivated to cause the element to re-engage the thread of the shaft. Movement of the carrier can then be driven in the normal manner.

A problem associated with disengaging the element entirely from the threaded shaft is that the element is either fully engaged or disengaged. As such, when the element is initially disengaged, the weight of the carrier may cause an inadvertent movement of the carrier as the weight of the carrier and any instruments attached to it are suddenly no longer supported by the tool holding mechanism and, for example, may be heavier than the user anticipated. In addition, movement to the carrier with the element disengaged increases the risk of other erroneous movements of the carrier. In surgical applications, erroneous movements of the carrier can be a serious safety concern (potentially causing injury to a patient or the surgeon).

It is an object of embodiments of the present invention to seek to ameliorate the problems associated with the prior art.

SUMMARY OF THE INVENTION

Accordingly, an aspect of the present invention provides a clutch mechanism for use with a carrier of a linear drive device, the mechanism comprising: a housing; a first gear coupled to the housing and having gear teeth configured to engage a threaded shaft of a linear drive device, such that rotation of the shaft causes the housing to move along the shaft in a first mode of, operation; and a first clutch arrangement associated with the first gear and configured to prevent substantial rotation of the first gear with respect to the housing when a rotational force applied to the first gear is less than a threshold force and to permit rotation of the first gear with respect to the housing when a rotational force applied to the first gear is greater than the threshold force, such that the housing can be manually moved along a length of the shaft, in a second mode of operation, by exerting a force on the housing such that the rotational force applied to the first gear through the interaction of the threaded shaft and the gear teeth exceeds the first threshold.

Preferably, the first clutch arrangement comprises a first clutch plate and a second clutch plate arranged to apply a compressive force on the first gear.

Advantageously, the first clutch plate is integrally formed with the housing and the second clutch plate may be moved with respect to the first clutch plate.

Conveniently, an adjustment mechanism is provided to vary the threshold force of the first gear.

Preferably, the adjustment mechanism comprises a user actuatable handle.

Advantageously, a resilient biasing element is provided to maintain the compressive force on the first gear.

Preferably, the mechanism further comprises a second gear coupled to the housing and having gear teeth configured to engage a shaft of a linear drive device, such that a path suitable to receive a shaft of a linear drive device is defined between the first and second gears.

Preferably, the second gear is substantially freely rotatable with respect to the housing.

Advantageously, the mechanism further comprises a second clutch arrangement associated with the second gear and configured to prevent substantial rotation of the second gear with respect to the housing when a rotational force applied to at least one of the gear teeth of the second gear is less than a threshold force and to permit rotation of the second gear with respect to the housing when a rotational force applied to the second gear is greater than the threshold force, such that the housing can be moved along the shaft by rotation of the shaft of a linear drive device in a first mode of operation and can be manually moved along a length of the shaft in a second mode of operation.

Another aspect of the present invention provides a linear drive device comprising: a threaded shaft; a motor coupled to the threaded shaft and configured to drive rotation of the threaded shaft; and a carrier fitted to the threaded shaft by a clutch mechanism.

Another aspect of the present invention provides, a surgical tool holding mechanism including a linear drive device or clutch mechanism.

Advantageously, the housing further comprises an attachment arrangement suitable to receive a surgical tool or instrument.

Preferably, the mechanism further comprises an endoscopic tool attached to the attachment arrangement.

Another aspect of the present invention provides a surgical tool holding mechanism configured to be coupled to a linear drive device, the surgical tool holding mechanism comprising: a clutch mechanism; and a carrier configured to be fitted to a threaded shaft of the linear drive device by the clutch mechanism, the clutch mechanism comprising:

a housing; a first gear coupled to the housing and having gear teeth configured to engage the threaded shaft of the linear drive device, such that rotation of the shaft causes the housing to move along the shaft in a first mode of operation; and a first clutch arrangement associated with the first gear and configured to prevent substantial rotation of the first gear with respect to the housing when a rotational force applied to the first gear is less than a threshold force and to permit rotation of the first gear with respect to the housing when a rotational force applied to the first gear is greater than the threshold force, such that the housing is manually moveable along a length of the shaft, in a second mode of operation, by exerting a manual force on the housing such that the rotational force applied to the first gear through the interaction of the threaded shaft and the gear teeth exceeds the first threshold.

The clutch mechanism may further include a second gear coupled to the housing and having gear teeth configured to engage the threaded shaft of the linear drive device, the first and second gears defining a path for the threaded shaft.

The second gear may be substantially free to rotate with respect to the housing.

The threshold force may be determined by a compressive force across two ends of the first gear.

The two ends of the first gear may be two ends which are not configured to engage the threaded shaft.

The two ends of the first gear may not include gear teeth configured to engage the threaded shaft.

The two ends of the first gear may oppose each other across a length of the first gear.

The first clutch arrangement may further include a resilient biasing element which is configured to apply the compressive force across the two ends of the first gear.

The housing may be formed of two parts which are coupled together.

The housing may include a cage portion in which the first gear is mounted and an extension portion in which a second gear is mounted.

The two parts of the housing in the region of the extension portion may be coupled together by engagement of respective hooked coupling members.

The clutch mechanism may further include a resilient biasing element configured to apply a compressive force to the first and second gears.

The hooked coupling members may be configured to permit a movement of the two parts of the housing towards each other and to inhibit decoupling of the two parts of the housing.

The first gear may be mounted for rotation about an axle and the resilient biasing element is mounted to the axle, the axle and resilient biasing element being configured to apply the compressive force across the first gear.

The housing may be formed from two substantially identical parts.

The carrier may be configured to be coupled to an endoscope.

The carrier may be configured to be coupled to an endoscopic tool.

The carrier may be configured to be coupled to a surgical tool.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

Embodiments of the present invention will now be described by way of example with reference to the accompanying drawings in which.

DETAILED DESCRIPTION OF THE INVENTION

Figure 1:
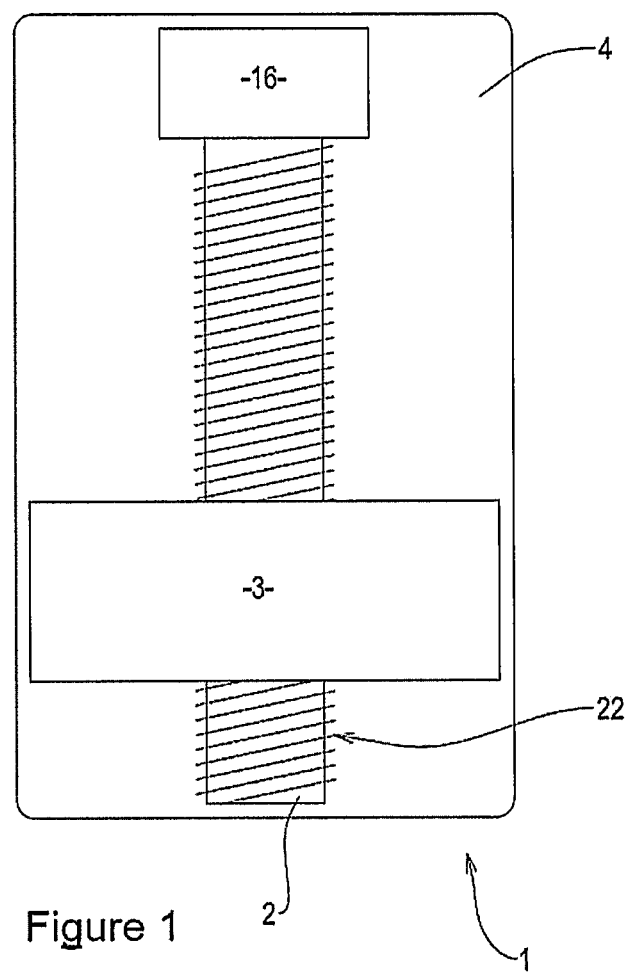
FIG. 1 shows a first view of a linear drive device including a clutch mechanism.

With reference to FIG. 1, an embodiment of the present invention comprises a linear drive device 1.

The linear drive device 1 comprises a threaded shaft 2 and a motor 16 coupled to the threaded shaft 2 such that activation of a motor 16 causes the threaded shaft 2 to rotate. Preferably, the motor 16 is coupled to a proximal end of the threaded shaft 2. This coupling may be achieved by the use of a gearbox (not shown) or through a direct coupling.

The threaded shaft 2 and motor 16 are fitted to a housing 4. The motor 16 is secured to the housing 4 and prevented from rotation with respect thereto. This may be achieved by, for example, the use of an adhesive, or one or more bolts. Alternatively, the motor 16 may have a casing (not shown) which is integrally formed with the housing 4. Other arrangements are also possible.

The threaded shaft 2 is free to rotate with respect to the housing 4 driven by the motor 16. In an embodiment, a bearing (not shown) is provided at a distal end of the threaded shaft 2 which supports the threaded shaft 2 with respect to the housing 4.

Figure 2:
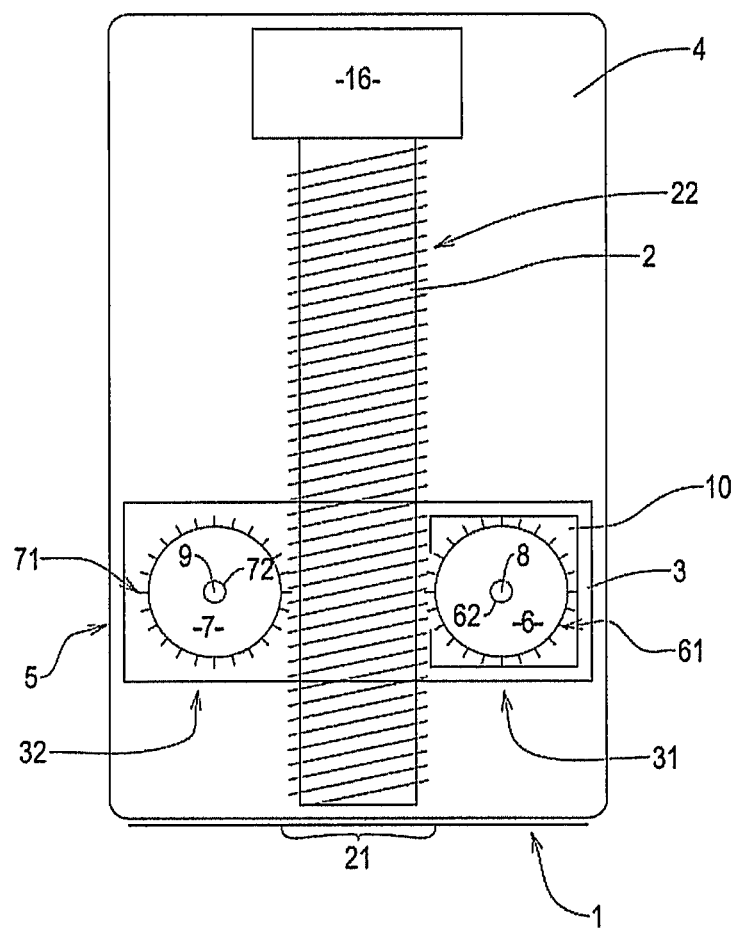
FIG. 2 shows a second view of a linear drive device including a clutch mechanism.
Figure 3:
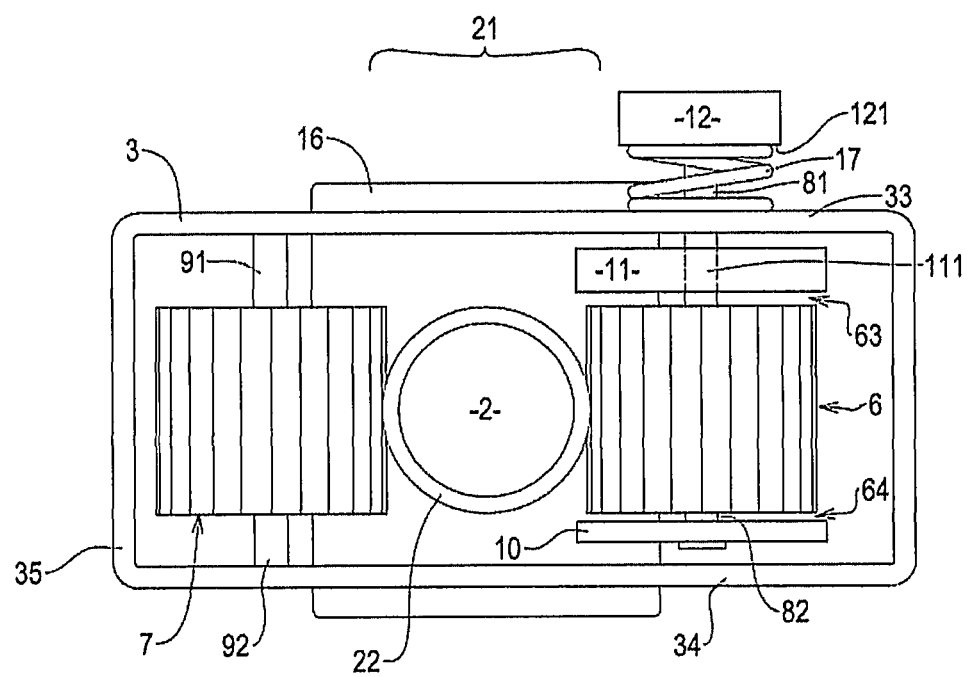
FIG. 3 shows the third view of a linear drive device including a clutch mechanism.

With reference to FIG. 2, a carrier comprising a housing 3 and a clutch mechanism 5 is provided. The housing 3 defines a first 31 and may define a second 32 cavity. Each cavity 31,32 may comprise a pair of walls 33,34 separated from each other by one or more spacers 35 (this can be best seen in FIG. 3).

As shown in FIG. 2, the clutch mechanism 5 is configured to be fitted to the housing 3 and comprises a first 6 and a second 7 gear. The first gear 6 is fitted within the first cavity 31 of the housing 3 (between the walls thereof 33,34) and the second gear 7 is fitted within the second cavity 32 of the housing 3 (between the walls thereof 33,34). A path 21 is defined between the first 6 and second 7 gears, the path 21 being configured to receive the threaded shaft 2 of the linear drive device 1.

The first 6 and second 7 gears have teeth 61,71 which are adapted to engage the thread 22 of the threaded shaft 2 of the linear drive device 1 received in the path 21 defined by the gears 6,7.

The first 6 and second 7 gears are mounted on respective axles 8,9. The axles 8,9 are fitted to the housing 3, and the first 6 and second 7 gears are each substantially free to rotate about a longitudinal axis of the associated axle 8,9. The axles 8,9 may be elongate members which pass through an orifice 62,72 in each of the gears 6,7; a length of the axles 8,9 may be greater than a length of the respective gear 6,7.

Rotational movement of the first gear 6 about the longitudinal axis of its axle 8 is restricted or restrained, for example, by a compressive force across two end faces 63,64 of the gear 6. This compressive force may be achieved through the use of a pair of clutch or brake plates 10,11 (or any other such member or mechanism).

Each clutch plate 10,11 is disposed adjacent a respective end face 63,64 of the first gear 6, and is configured to apply a force to the respective end face 63,64 of the gear 6. The clutch plates 10,11 are located within the first cavity 31 of the housing 3 along with the first gear 6. The arrangement is such that the clutch plates 10,11 are generally parallel to the walls 33,34 of the cavity 31.

The compressive force applied to the first gear 6 can be adjusted through the use of an adjustment mechanism.

For example, in an embodiment, a first end of the axle 8 passes through a hole 111 defined by the first clutch plate 11 adjacent a first end face 63 of the gear 6 and out of the first cavity 31 of the housing 3. A handle 12 is secured to the first end 81 of the axle 8.

A resilient biasing element 17 (for example, a helical spring) is provided—which may form part of the adjustment mechanism. The resilient biasing element 17 is provided to bias apart an inner surface 121 of the handle 12 and an outer surface of one of the walls 33 of the housing 3. In this embodiment, the handle 12 may be secured to the axle 8 such that it is not operable to move along a length of the axle 8.

A second end 82 of the axle 8 (opposing the first end 81 of the axle 8 across a length of the axle 8) extends through a second end face 64 of the gear 6 (which opposes the first end face 63 of the gear 6 across a length of the gear 6) and into a second clutch plate 10.

The axle 8 is preferably prevented from rotation about its longitudinal axis with respect to the housing 3 by, for example, the use of a keyed section at the second end 82 of the axle 8—wherein the keyed section of the axle 8 is configured to fit a correspondingly keyed section of the second clutch plate 10 and the clutch plate 10 is keyed with the first cavity 31 of the housing 3 (to prevent relative rotational movement)—for example, by abutment with one or more of the cavity spacers 35.

In addition, the second end 82 of the axle 8 is secured to the second clutch plate 10 such that a linear movement of the axle 8 with respect to the first cavity 31 of the housing 3 causes a corresponding linear movement of the second clutch plate 10.

The first clutch plate 11 is configured to abut an inner surface of one of the walls 33 of the first cavity 31 and the first end face 63 of the gear 6.

Thus, the resilient biasing element 17 biases the second clutch plate 10 (through the axle 8) such that a force is applied to the second end face 64 of the gear 6. This causes the first end face 63 of the gear 6 to abut the first clutch plate 11 which is prevented from further movement (in a direction parallel to the longitudinal axis of the axle 8 and away from the gear 6) by the inner surface of one of the walls 33 of the first cavity 31 of the housing 3 (which it also abuts). As such, a compressive force is applied to the first 63 and second 64 end faces of the gear 6.

The compressive force applied to the gear 6 by the two clutch plates 10,11 defines a threshold force which must be applied to the teeth 61 of the first gear 6 in order to cause the first gear 6 to rotate about its axle 8.

The second gear 7 is mounted on its axle 9 and is free to rotate about a longitudinal axis of the axle 9. First 91 and second 92 ends of the axle 9 may be fitted to the housing 3 (the fitting may include the use of bearings—not shown).

The first clutch plate 10 may be integrally formed with the housing 3.

Figure 4:
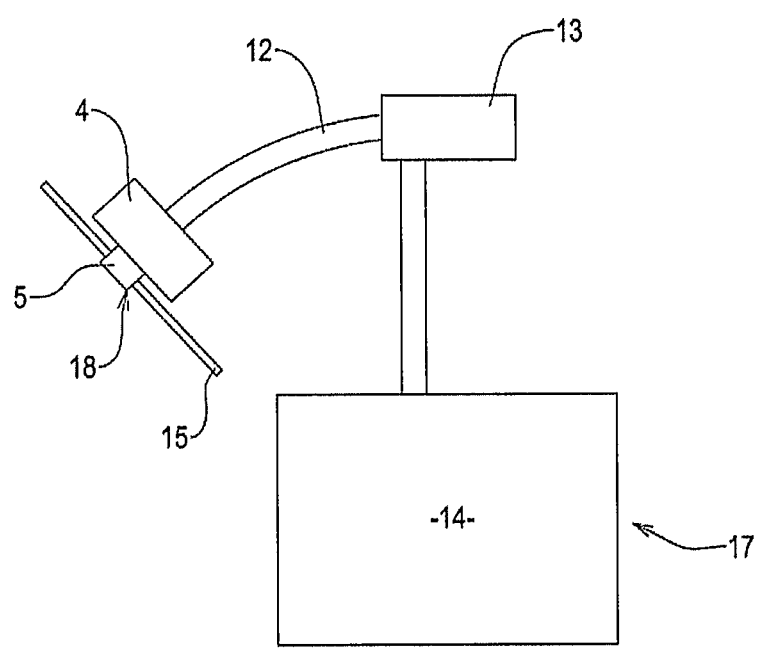
FIG. 4 shows a mechanism including a linear drive device and clutch mechanism.

An attachment arrangement 18 may be mounted on or attached to the carrier (for example to the housing 3) and may be configured to receive a tool or instrument. For example, the attachment arrangement may be suitable to receive an endoscope or endoscopic surgical tool 15—as shown in FIG. 4.

The linear drive device 1 is, in some embodiments, mounted on an arm 12. The arm 12 is, in turn, mounted on a member 13 which may permit and drive rotational motion of the member 13 and an arm 12 about a support which forms part of a robot body 14.

Together, the linear drive device 1, the arm 12, the member 13 and the robot body 14 (or any sub-combination of these features) may be considered to form a robot 17 (or another type of mechanism) which may be a surgical robot (or other type of surgical tool holding mechanism). The surgical robot is, in some embodiments, an endoscopic surgical assistant robot (or tool holding mechanism) configured to assist a surgeon during an endoscopic surgical operation by, for example, supporting an endoscope 15 or other tools.

Figure 5:
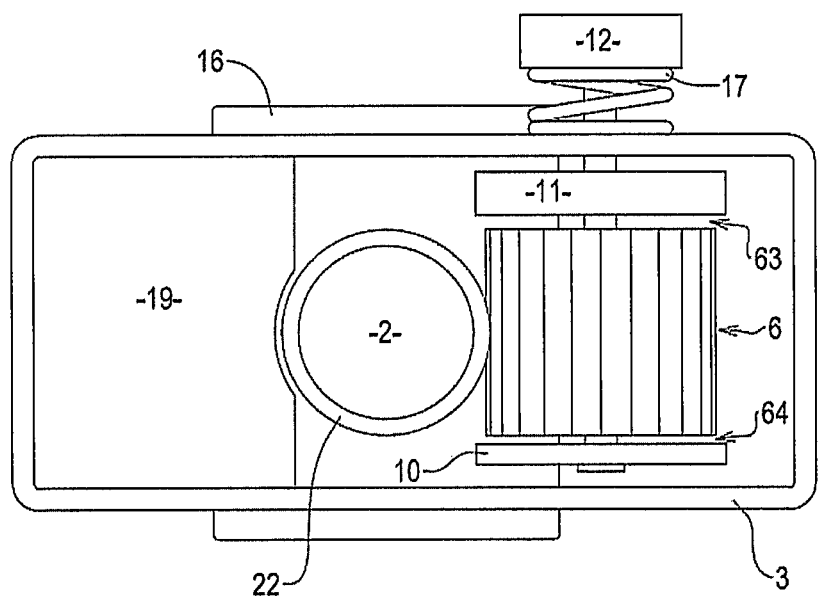
FIG. 5 shows a first view of a linear drive device including a clutch mechanism.

In embodiments (see FIG. 5), the second gear 7 is not provided and instead a substantially smooth support surface configured to slide over the thread 22 of the threaded shaft 2 may be provided. This support surface may form part of an abutment block 19 positioned in generally the same location as the above described second gear 7. Thus, the above described path 21 is defined between the abutment block 19 and the first gear 6.

In operation, movement of the carrier (i.e. the housing 3 and clutch mechanism 5) can be achieved by actuating the motor 16 to cause rotation of the threaded shaft 2. As the threaded shaft 2 rotates, the thread 21 of the shaft 2 cooperates with the teeth 61,71 of the first gear 6 and the second gear 7. As the first gear 6 is held such that it is prevented or is substantially prevented from rotation by the compressive force applied thereto, the carrier is driven along a length of the threaded shaft 2 (as is conventional, the carrier is prevented from rotation with respect to the motor 16).

The second gear 7 substantially freely rotates during this movement of the carrier.

Movement of the carrier along the threaded shaft 2 can be achieved in this manner under the control of the motor 16 (which may be controlled be the robot 17).

When a larger linear movement of the carrier is desired, then a user may grasp the carrier housing 3 and manually push or pull the carrier along the length of the shaft 2 as desired. When this occurs, the threshold force defined by the compression force applied by the two clutch plates 10,11 (for example) to the first gear 6 is overcome. The first gear 6 rotates about the longitudinal axis of its axle 9 and the carrier may be moved up or down the shaft 2. When the desired location along the length of the shaft 2 is reached by the carrier, the user releases the carrier and the force applied to the teeth 61 of the first gear 6 once again falls below the threshold force required to cause rotation of the first gear 6 about the longitudinal axis of its axle 9. As such, the carrier is held in that location along the length of the shaft 2.

Movement of the carrier driven by the motor 16 is a first mode of operation and movement of the carrier by manual action is a second mode of operation. The two modes of operation do not occur simultaneously.

As will be appreciated, this arrangement may ameliorate the issues discussed above in relation to the prior art. Specifically, the clutch mechanism 5 can help to reduce the risk of erroneous movements of the carrier (and anything attached thereto).

In the above described embodiment, a user may be able to apply a force to the handle 12 in the direction of the housing 3 against the force of the resilient biasing element 17. This action results in a reduction in the compressive force applied to the gear 6 and, hence, reduces the threshold force—to allow more easy movement of the carrier along the shaft 2. Alternatively, the handle 12 may be enclosed by the housing 3 and inaccessible to the user.

Figure 6:
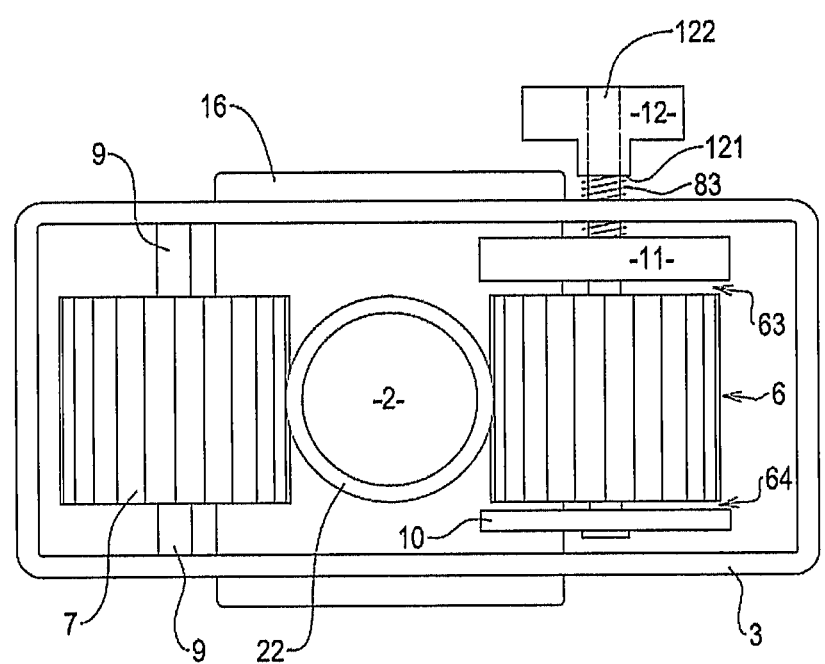
FIG. 6 shows a first view of a linear drive device including a clutch mechanism.

In an embodiment (best seen in FIG. 6), the adjustment mechanism may not include a resilient biasing element 17. For example, the handle 12 may be coupled to the axle 8 by a threaded portion 83 at the first end 81 thereof. A corresponding thread may be provided in an axle receiving hollow 122 in the handle 12. This allows the handle 12 to be secured to the threaded 83 portion of the axle 8 by mounting the axle receiving hollow 122 of the handle 12 on the threaded portion 83 of the axle 8 such that the threads mate. The handle 12 is located outside of the first cavity 31 of the housing 3 and the inner surface 121 of the handle 12 is configured to abut the outer surface of one of the walls 33 of the housing 3. Rotation of the handle 12 causes the handle 12 to move along the threaded portion 83 of the axle 8 (towards or away from the first end face of the gear 6—depending on the direction of rotation). When the handle 12 is rotated such that the inner surface 121 of the handle 12 abuts the outer surface the wall 33 of the housing 3, further rotation of the handle 12 (in the same direction) causes the axle 8 to be drawn into the handle 12. This causes the second clutch plate 10 to apply a force to the second end face 64 of the first gear 6. Thus, a compressive force is applied to the gear 6 substantially as described above.

Figure 7:
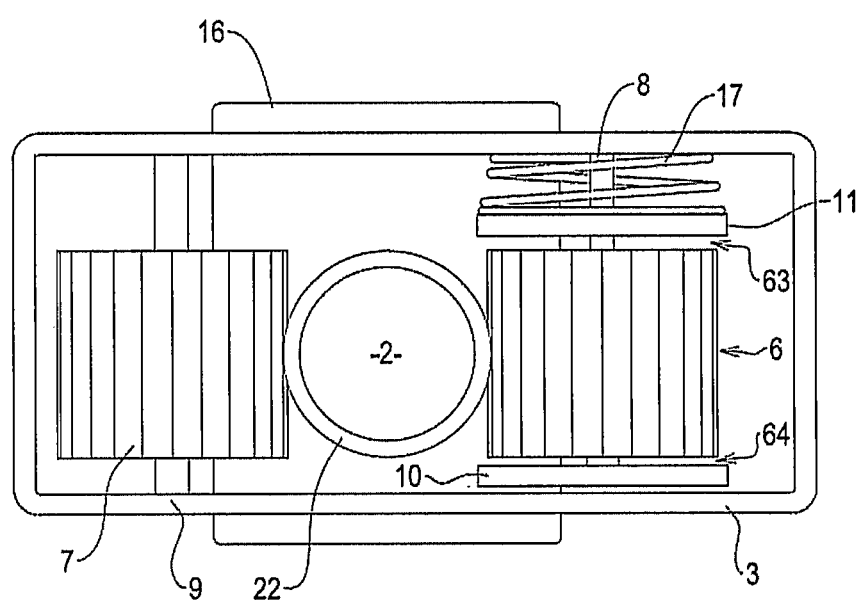
FIG. 7 shows a first view of a linear drive device including a clutch mechanism.

In an embodiment (best seen in FIG. 7), a resilient biasing element 17 is provided to bias the first clutch plate 11 away from an inner surface of one of the walls 33 of the housing 3. The second clutch plate 10 is located within the first cavity 31 of the housing 3 adjacent a wall 34 of the housing 3 and the second end face 64 of the gear 6. Thus, the resilient biasing element 17 applies a force on the first clutch plate 11 which abuts the first end face 63 of the gear 6 and presses the second end face 64 of the gear 6 against the second clutch plate 10 (which, in turn, is pressed against an inner surface of one of the walls 34 of the cavity 31 of the housing 3). In this manner a compressive force is applied to the gear 6.

Figure 8:
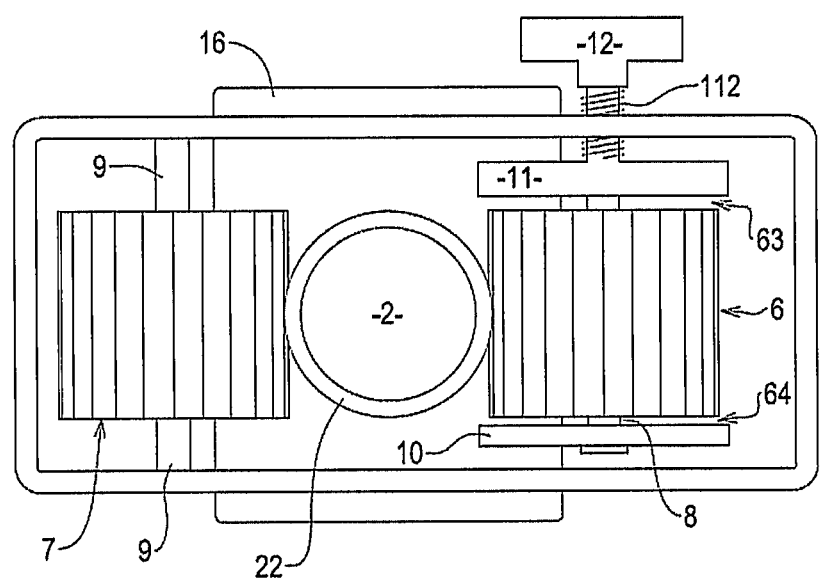
FIG. 8 shows a first view of a linear drive device including a clutch mechanism.
Figure 9:
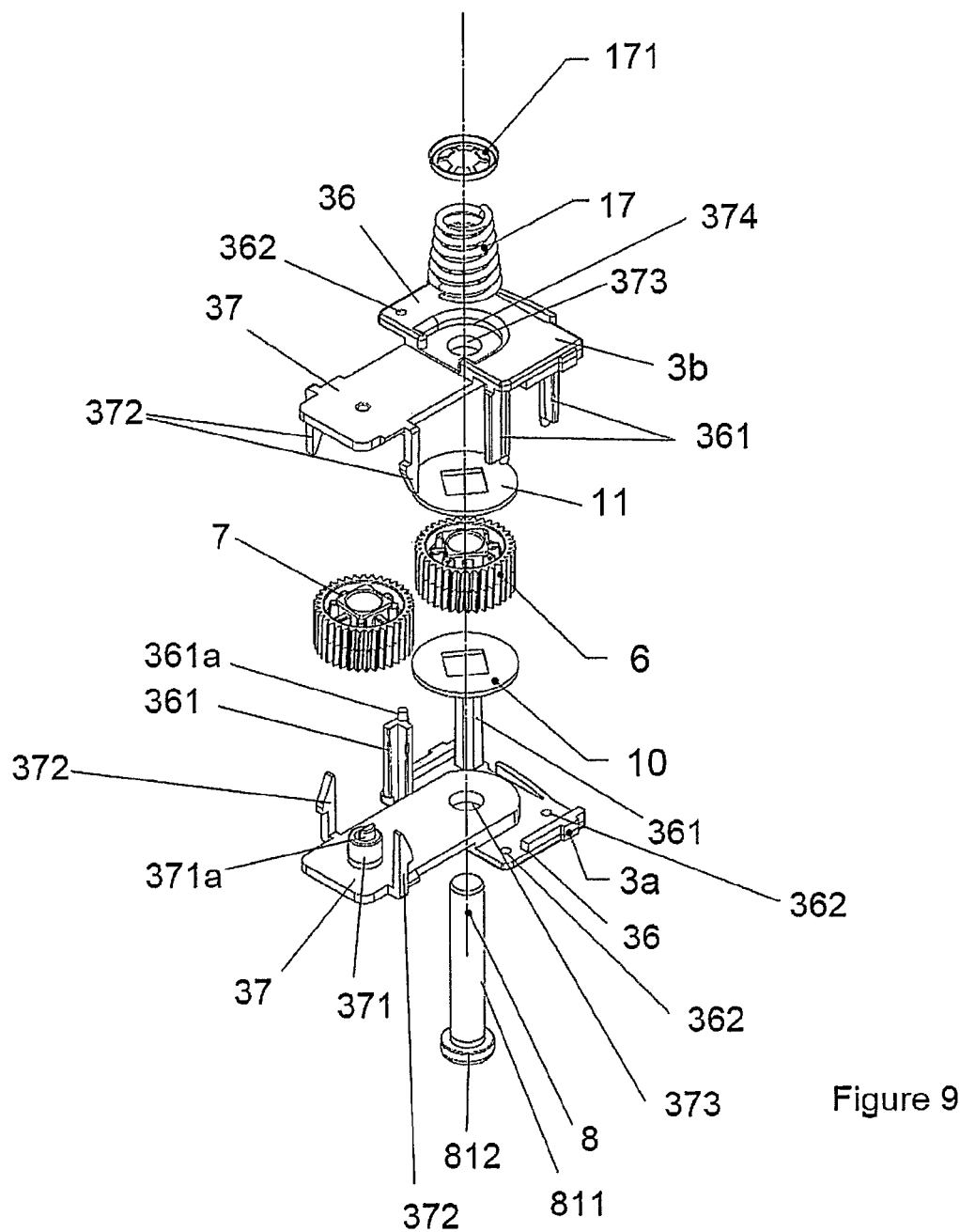
FIG. 9 shows an exploded diagram of an embodiment.
Figure 10:
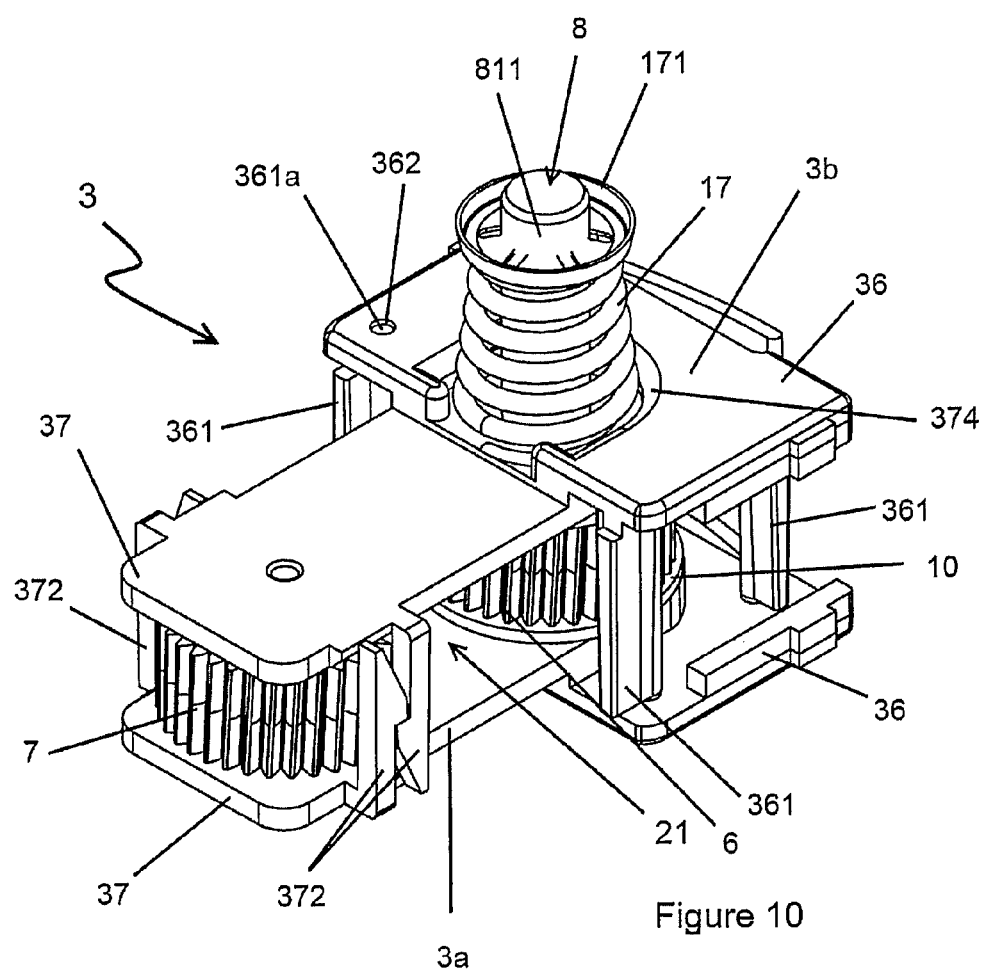
FIG. 10 shows a perspective view of an embodiment.
Figure 11:
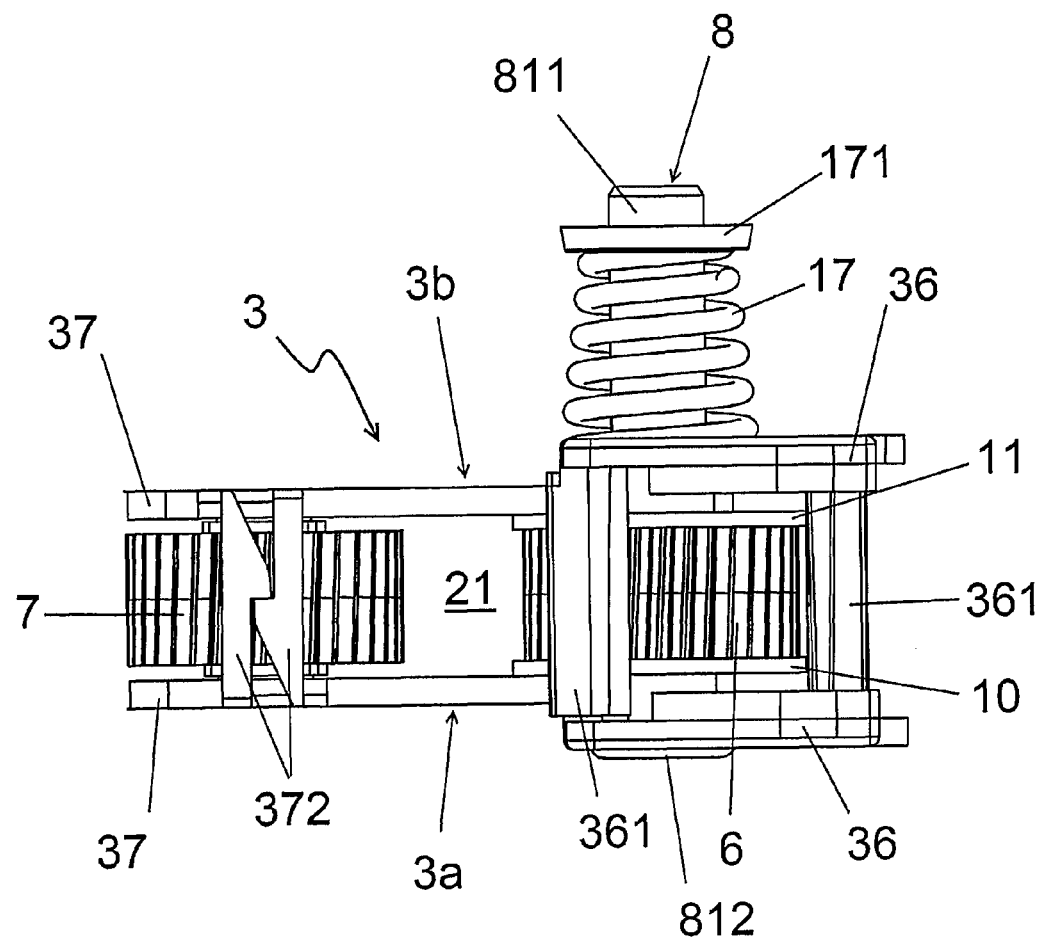
FIG. 11 shows a side view of an embodiment.
Figure 12:
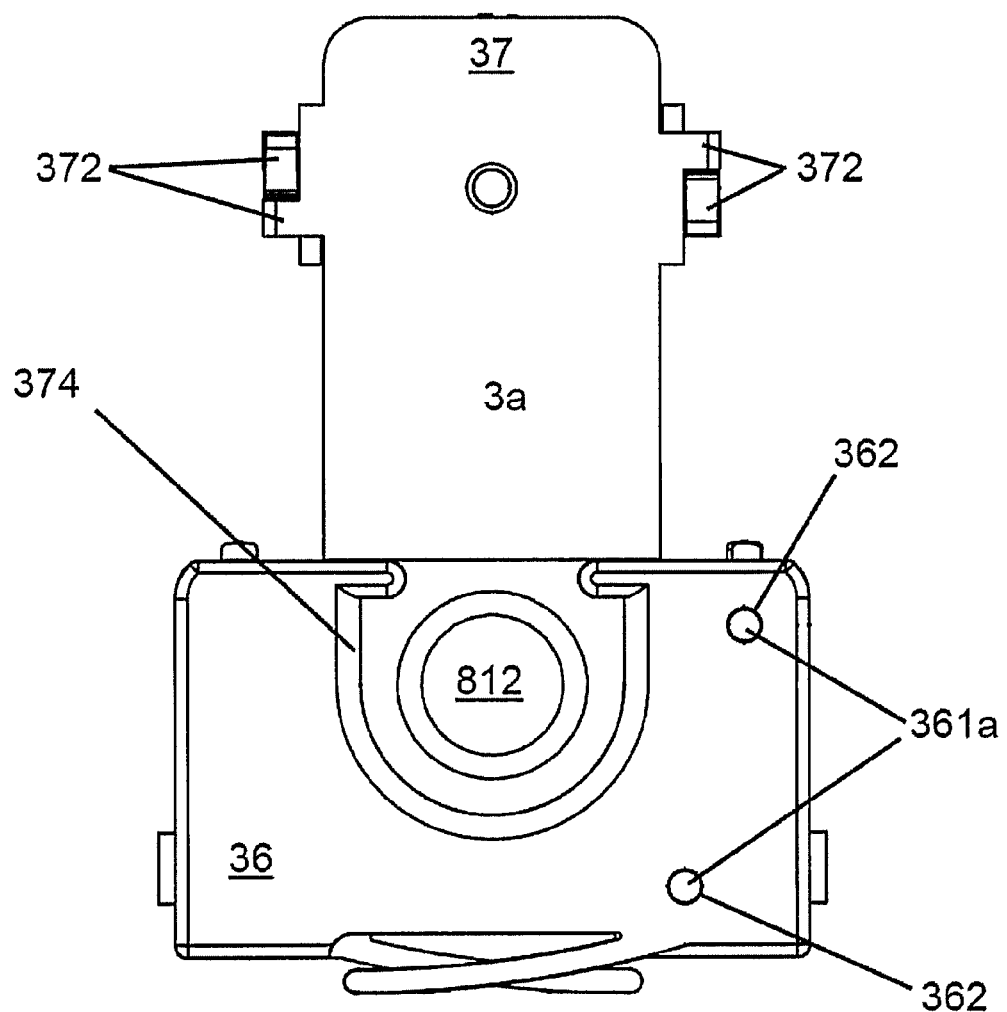
FIG. 12 shows a bottom view of an embodiment.
Figure 13:
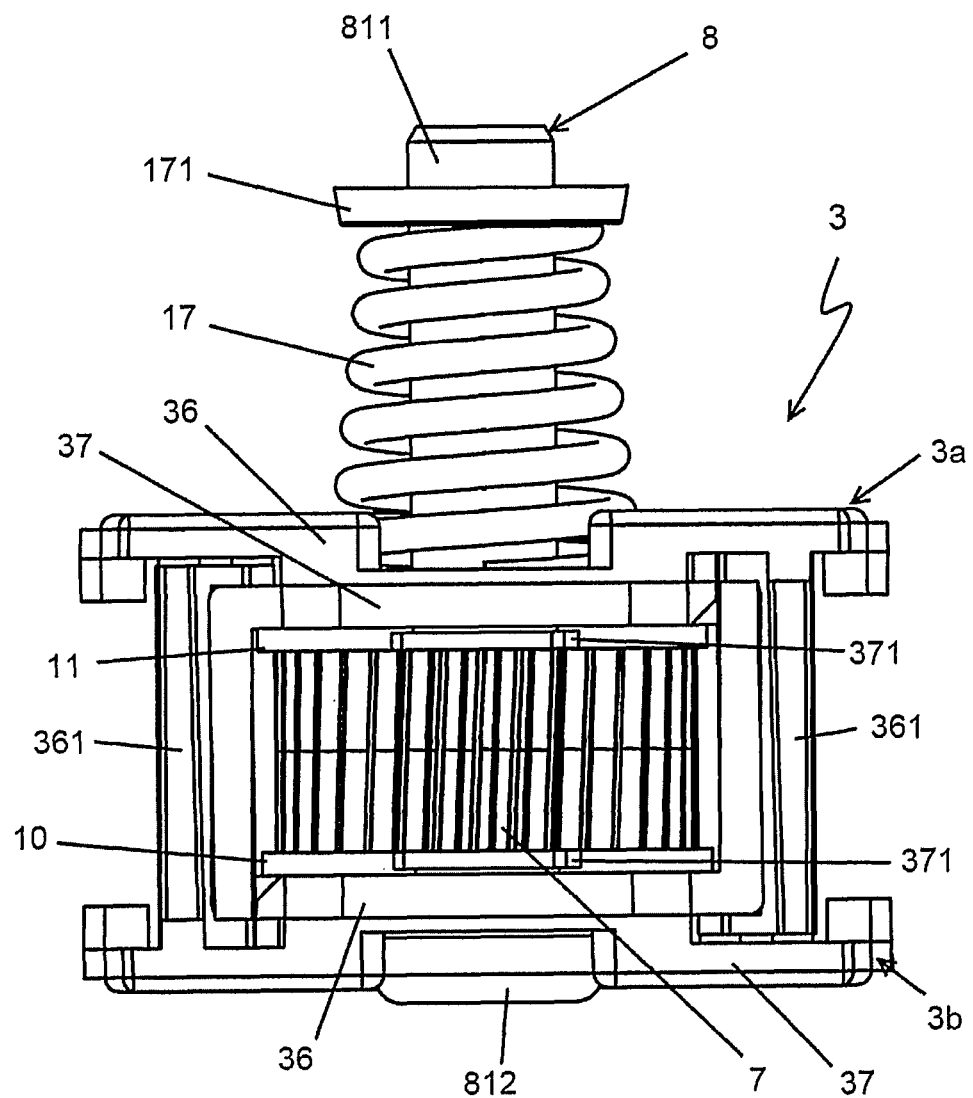
FIG. 13 shows an end view of an embodiment.

In an embodiment (best seen in FIG. 8), the wall 33 of the housing 3 is configured to receive a threaded element 112 of the first clutch plate 11 in a correspondingly threaded hole defined by the wall 33 of the housing. In this embodiment, rotation of the handle 12 may be used to force (or press) the first clutch plate 11 against the first end face 63 of the gear 6 to apply a compressive force (in combination with the second clutch plate 10) substantially as described above.

In this and similar embodiments, the axles 8,9 may each comprise two separate elongate members secured so as to extend from opposing end faces of the gears 6,7. Alternatively, each of the axles 8,9 may be integrally formed with each respective gear 6,7.

As will be appreciated, different instruments or tools may be attached to the housing 3 of the carrier and, therefore, the total weight of the carrier and tools may vary. As such, the handle 12 can be used to vary the compressive force applied to the first gear 6 such that the threshold force is altered. A higher compressive force on the first gear 6 means a higher threshold force required to cause rotation of the first gear 6 about the longitudinal axis of its axle 8.

In addition, during setup of a robot 17 including such a linear drive device 1 and clutch mechanism 5, the handle 12 can be adjusted so as to decrease the compressive force applied to the first gear 6 considerably thus allowing easy movement of the carrier along the threaded shaft 2. When the desired setup location is reached, the handle 12 can be adjusted to increase the compressive force applied by the clutch plates 10,11 (for example) on the first gear 6. Thus, the carrier is secured in the desired location.

The use of the axle 9, clutch plates 11,12 and handle 12 in relation to the first gear 6 are just one example implementation of a biasing mechanism which defines a threshold force which must be applied to the teeth of the first gear 6 in order to cause rotation of the gear 6 about the longitudinal axis of its axle 8. Other arrangements may not require clutch or brake plates. Instead, other mechanisms may be utilised to define a threshold force.

It is envisaged that the second gear 7 may, in some embodiments, be provided with a clutch mechanism which may be the same or identical to the clutch mechanism 5 associated with the first gear 6. As such, the clutch mechanism 5 may comprise a first clutch arrangement associated with the first gear 6 and a second clutch arrangement associated with the second gear 7.

With reference to FIGS. 9 to 13, an embodiment includes a carrier having a housing 3 and a clutch mechanism 5 similar to the embodiments of FIGS. 1 to 8. The housing 3 is configured to receive the threaded shaft 2 and carries a pair of gears 6,7 which define a path 21 therebetween for receipt of the threaded shaft 2.

The housing 3 comprises a first part 3a and a second part 3b. The first and second parts 3a,3b are configured to engage each other to form the housing 3. In embodiments, the first and second parts 3a,3b of the housing 3 are substantially identical.

The first part 3a may have a cage portion 36 and an extension portion 37. In some embodiments, the cage portion 36 and extension potion 37 overlap each other. The cage portion 36 includes one or more pillars 361 and may include two or more such pillars 361. Each pillar 361 may comprise a two parts each substantially perpendicular to the other such that the pillar 361 has an L-shaped cross-section.

The or each pillar 361 includes a column 361a at a distal end thereof.

The cage portion 36 may also define one or more column receiving apertures 362 (and may include two or more such apertures 362). The number of column receiving apertures 362 may be equal to the number of columns.

In embodiments, the cage portion 36 includes one or more pillars 361 and one or more column receiving apertures 362 such that they oppose each other across a part of the cage portion 36.

The extension portion 37 extends from the cage portion 36 with a longitudinal axis substantially perpendicular to a longitudinal axis of the cage portion 36. The extension portion 37 may be a raised platform with respect to the cage portion 36 such that a plane of the extension portion 37 is substantially parallel to a plane of the cage portion 36.

The extension portion 37 includes an integral axle portion 371 which is configured to be received by an axle receiving aperture 71 defined by the gear 7. The integral axle portion 371 may include a keyed end section 371a which is configured to mate with another correspondingly configured integral axle portion 371 to form an axle.

The extension portion 37, at a part generally remote from the cage portion 36, includes one or more hooked coupling members 372. In embodiments, there are two hooked coupling members 372 which are positioned on opposing sides of the extension portion 37. In such embodiments, there are at least two hooked coupling members 372 which have hook extensions which extend in opposing directions with respect to each other. In some embodiments, a first of the two hooked coupling members 372 has a hook portion extending towards the cage portion 36 and a second of the two hooked coupling members 372 has a hook portion extending away from the cage portion 36. The or each hooked coupling member 372 extends from the extension portion 37 to a height which may be less than a height of the pillar 361. The or each hooked coupling members 372 generally extend in the same direction as the or each pillar 361.

The extension portion 37 also defines a shaft receiving aperture 373 through an entire depth of the part 3a,3b of the housing 3 in a section of the extension portion 37 which is located generally within the cage portion 36. The shaft receiving aperture 373 is configured to receive at least part of a shaft or axle 8.

An outer face of the part 3a,3b which opposes an inner face of the part (the inner face being the face from which the pillars 361 and hooked coupling members 372 extend) may include a recess 374. The recess 374 may be substantially circular in shape and a part of the recess 374 may be open at the side. In embodiments, the recess 374 is substantially D-shaped with the open side being the straight side. In such embodiments, protrusions may be provided to help to hold one or more items within the recess 374.

The two gears 6,7 have teeth which are configured to engage the thread 22 of the threaded shaft 2.

One of the gears 7 is configured to be mounted on the integral axle portion 371 of the part 3a,3b of the housing 3 and, therefore, defines a bore suitable to receive at least part of the integral axle portion 371.

Another of the gears 6 is configured to be mounted on a shaft or axle 8. Clutch plates 10,11 are also configured to be mounted on the shaft or axle 8 either side of the gear 6. Each clutch plate 10,11 may be substantially circular in outer shape and may define an aperture configured to receive at least part of the shaft or axle 8. The aperture may have a shape which is keyed to a corresponding protrusion which extends form an end of the gear 6 such that, when fitted together, the clutch plate 10,11 rotates with the gear 6 with respect to the housing 3. In embodiments, both ends of the gear 6 include such protrusions. In other embodiments, the clutch plates 10,11 are configured such that the gear 6 rotates with respect to the clutch plates 10,11 and housing 3.

A resilient biasing element 17 is provided and this may be a conical spring. The resilient biasing element 17 may be configured to receive at least part of the shaft or axle 8 and is mounted thereto in some embodiments.

In embodiments, a clip 171 is also provided. The clip 171 is configured to be mounted on the shaft or axle 8. In embodiments, the clip 171 is configured to grip the shaft or axle 8 along a length thereof and, in embodiments, the clip 171 is configured to grip the shaft or axle 8 such that its position along the length of the shaft or axle 8 does not move substantially under the forces normally experienced during use. The clip 171 may be a star washer. The clip 171 may be used, in embodiments, to compress the resilient biasing element 17 between the clip 171 and the housing 3.

The shaft or axle 8 may comprise a general cylindrical body 811 with a head 812 located at one end of the body 811—the head 812 having a larger diameter than the body 811. The head 812 may be configured for receipt (at least in part) by the recess 374.

Accordingly, the first part 3a of the housing 3 may be provided. One of the gears 7 may be located on the integral axle portion 371 of that part 3a. The shaft or axle 8 may be provided and inserted into the shaft receiving aperture 373 of the first part 3a such that the head 812 of the shaft or axle 8 is at least partially received by the recess 374 of the first part 3a of the housing 3.

A clutch plate 10 may be mounted on the shaft or axle 8 such that it rests on the inner face of the part 3a of the housing 3. Another of the gears 6 may be mounted on the shaft or axle 8 such that an end of the gear 6 rests on the clutch plate 10.

Another clutch plate 11 may be mounted on the shaft or axle 8 such that it rests on another end of the gear 6 (such that that gear 6 is sandwiched between the two clutch plates 11).

The second part 3b of the housing 3 may be mounted on the shaft or axle 8 such that the shaft receiving aperture 373 of the second part 3b receives at least part of the shaft or axle 8.

The second part 3b may be moved with respect to the first part 3a such that the or each column 361a of the first part 3a is received by a corresponding column receiving aperture 362 of the second part 3b, and vice versa.

The or each hooked coupling member 372 of the first part 3a engages a respective one of the hooked coupling members 372 of the second part 3b such that the hook portions of each hooked coupling member engage to inhibit separation of the two parts 3a,3b of the housing 3.

The integral axle portion 371 of the second part 3b of the housing 3 may also be received by the gear 7. In embodiments, the two integral axle portions 371 (one of the first part 3a and one of the second part 3b) form an axle about which the gear 7 is substantially free to rotate. Keyed sections 371a of the two integral axle portions 371 may engage or otherwise interact in the formation of the axle.

The resilient biasing element 17 may be mounted on a part of the shaft or axle 8 which extends through the second part 3b of the housing 3. At least a part of the resilient biasing element 17 is received by the recess 374 of the second part 3b of the housing 3. Movement of the resilient biasing element 17 laterally across the second part 3b is inhibited by the recess 374.

The clip 171 may be positioned on the shaft or axle 8 and moved down the shaft or axle 8 to compress the resilient biasing element 7 and, therefore, adjust the compressive force which is applied across the gear 6 by the clutch plates 10,11.

The two parts 3a,3b of the housing 3 are permitted a degree of freedom of movement with respect to each other (generally along the axis of the shaft or axle 8). Thus, the or each column 361 may move further into or out of its respective column receiving aperture 362.

The two parts 3a,3b are, in embodiments, held together by the shaft or axle 8, the resilient biasing element 17, and the clip 171. The two parts 3a,3b may be further held together by the engagement of the respective hooked coupling members 372.

The construction of some embodiments of the invention allows relative movement between the two parts 3a,3b of the housing such that the compressive force applied across the clutched gear 6 can be calibrated and set easily. The substantially identical parts 3a,3b mean that there are reduced construction costs and fewer different parts compared to other examples.

The term "robot" has been used above as an example of a mechanism which may hold a tool. References to "a robot" apply equally to other tool holding mechanisms. Similarly, a "surgical robot" is an example of a surgical tool holding mechanism and references to "a surgical robot" apply equally to other surgical tool holding mechanisms.

When used in this specification and claims, the terms "comprises" and "comprising" and variations thereof mean that the specified features, steps or integers are included. The terms are not to be interpreted to exclude the presence of other features, steps or components.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A surgical tool holding mechanism configured to be coupled to a linear drive device, the surgical tool holding mechanism comprising:
   a clutch mechanism; and
   a carrier configured to be fitted to a threaded shaft of the linear drive device by the clutch mechanism, the clutch mechanism comprising:
      a housing;
      a first gear coupled to the housing and having gear teeth configured to engage the threaded shaft of the linear drive device, such that rotation of the shaft causes the housing to move along the shaft in a first mode of operation; and
      a first clutch arrangement associated with the first gear and configured to prevent substantial rotation of the first gear with respect to the housing when a rotational force applied to the first gear is less than a threshold force and to permit rotation of the first gear with respect to the housing when a rotational force applied to the first gear is greater than the threshold force, such that the housing is manually moveable along a length of the shaft, in a second mode of operation, by exerting a manual force on the housing such that the rotational force applied to the first gear through the interaction of the threaded shaft and the gear teeth exceeds the first threshold, wherein:
      the threshold force is determined by a compressive force across two ends of the first gear,
      the first clutch arrangement further includes a resilient biasing element which is configured to apply the compressive force across the two ends of the first gear,
      the housing is formed of two parts which are coupled together, and
      the two parts of the housing in the region of the first gear are coupled together by engagement of respective hooked coupling members.

2. The surgical tool holding mechanism according to claim 1, wherein the clutch mechanism further includes a second gear coupled to the housing and having gear teeth configured to engage the threaded shaft of the linear drive device, the first and second gears defining a path for the threaded shaft.

3. The surgical tool holding mechanism according to claim 2, wherein the second gear is substantially free to rotate with respect to the housing.

4. The surgical tool holding mechanism according to claim 1, wherein the two ends of the first gear are two ends which are not configured to engage the threaded shaft.

5. The surgical tool holding mechanism according to claim 1, wherein the two ends of the first gear do not include gear teeth configured to engage the threaded shaft.

6. The surgical tool holding mechanism according to claim 1, wherein the two ends of the first gear oppose each other across a length of the first gear.

7. The surgical tool holding mechanism according to claim 1, wherein the housing includes a cage portion in which the first gear is mounted and an extension portion in which a second gear is mounted.

8. The surgical tool holding mechanism according to claim 7, wherein the respective hooked coupling members are positioned in the region of the extension portion.

9. The surgical tool holding mechanism according to claim 8, wherein the resilient biasing element is configured to apply the compressive force to the first and second gears.

10. The surgical tool holding mechanism according to claim 8, wherein the hooked coupling members are configured to permit a movement of the two parts of the housing towards each other and to inhibit decoupling of the two parts of the housing.

11. The surgical tool holding mechanism according to claim 10, wherein the first gear is mounted for rotation about an axle and the resilient biasing element is mounted to the axle, the axle and resilient biasing element being configured to apply the compressive force across the first gear.

12. The surgical tool holding mechanism according to claim 1, wherein the two parts of the housing are substantially identical parts.

13. The surgical tool holding mechanism according to claim 1, wherein the carrier is configured to be coupled to an endoscope.

14. The surgical tool holding mechanism according to claim 1, wherein the carrier is configured to be coupled to an endoscopic tool.

15. The surgical tool holding mechanism according to claim 1, wherein the carrier is configured to be coupled to a surgical tool.

\* \* \* \* \*